Oct. 14, 1958 E. S. BOERNER Plant Pat. 1,762
ROSE PLANT
Filed March 3, 1958
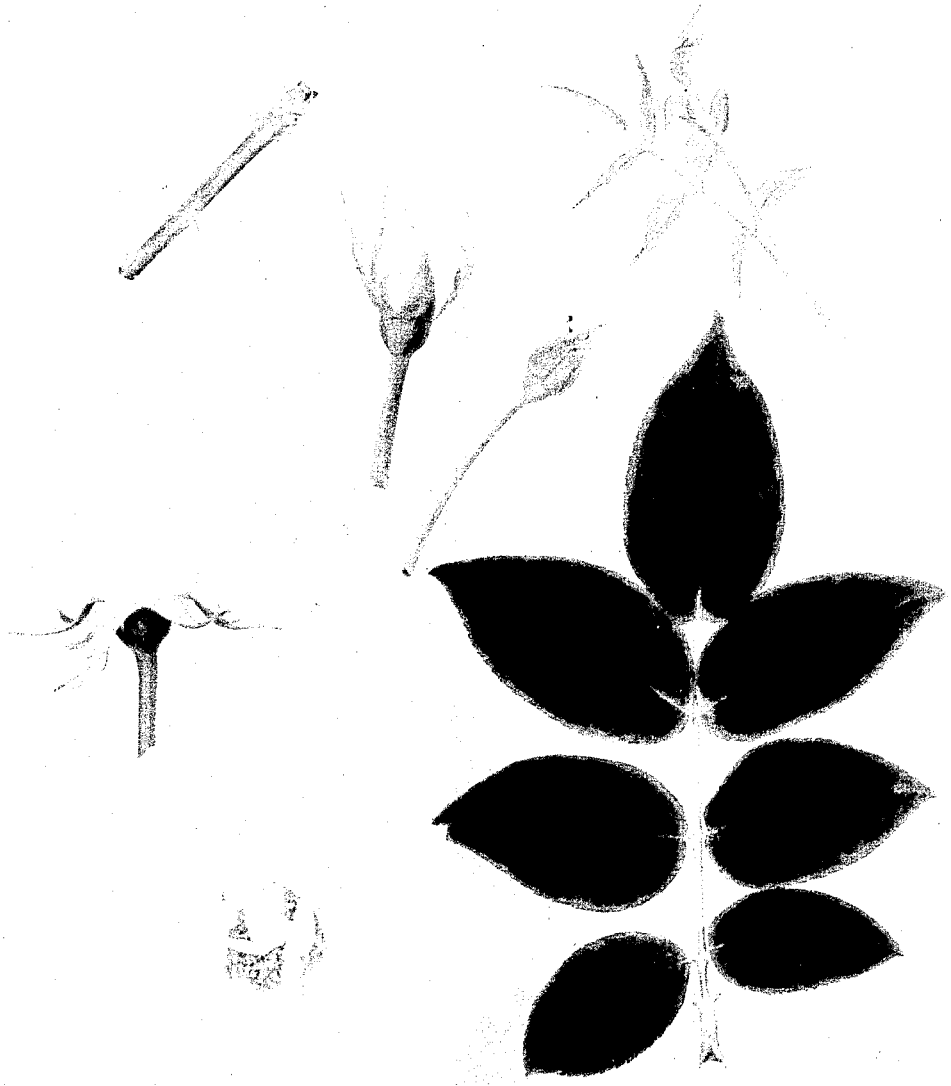
Inventor.
E. S. Boerner
By: Robb & Robb
Attorneys.

United States Patent Office

Plant Pat. 1,762
Patented Oct. 14, 1958

1,762

ROSE PLANT

Eugene S. Boerner, Newark, N. Y., assignor to Jackson & Perkins Company, Newark, N. Y., a corporation of New York Application March 3, 1958, Serial No. 718,932

1 Claim. (Cl. 47—61)

The present invention relates to a new and distinct variety of rose plant of the hybrid tea class, which was originated by me by crossing an unnamed and unpatented seedling of the hybrid tea rose "Starlite" (Plant Patent No. 414) which an unnamed and unpatented seedling of the floribunda rose "Glacier" (Plant Patent No. 1,025).

The primary objective of this breeding was to produce an improved white hybrid tea rose having thicker petals, combined with prolific blooming qualities characteristic of the parent "Starlite." This objective was fully achieved, along with other desirable improvements, as evidenced by the following unique combination of characteristics which are outstanding in the new variety, and distinguish it from its parents, as well as from all other varieties of which I am aware:

(1) Profuse production of blooms;
(2) Firm, thick and full flower petals;
(3) A distinctive and new White flower color, accompanied by a faint touch of cream in the center of the open flowers;
(4) Many light-colored thorns; and
(5) Exceptional suitability for garden use.

Asexual reproduction of the new variety, by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—An unnamed seedling of "Starlite."
*Pollen parent.*—An unnamed seedling of "Glacier."
Classification:
*Botanic.*—Hybrid tea.
*Commercial.*—Hybrid tea.

*Flower*

(Observations made from specimens grown outdoors at Newark, New York, in the early afternoon near the middle of September.)

Blooming habit: Recurrent—continuous and profuse.
Bud:
*Size.*—Large.
*Form.*—Long; is not affected by wet or hot weather.
*Color.*—When sepals first divide—Pale Dull Green-Yellow, Plate 17. When petals begin to unfurl—Sea-foam Green, Plate 31. When half-blown: inside of petals—White, Plate 53; reverse of petals—White, Plate 53, lightly overcast with Sea-foam Green, Plate 31.
*Sepals.*—Branched; curl back when petals begin to unfurl. Color: inside—Pale Fluorite Green, Plate 32; outside—Biscay Green, Plate 17.
*Calyx.*—Color—Biscay Green, Plate 17. Shape—apple. Size—large. Aspect—smooth. Odor when rubbed—none.
*Peduncle.*—Length — medium. Aspect — prickly. Strength—erect; heavy. Color—Oil Green, Plate 5.
*Opening.*—Opens up well; is not affected by adverse weather conditions.

Bloom:
*Size.*—Large. Average size when fully expanded—5 inches.
*Borne.*—Both singly and several together.
*Stems.*—Medium length; strong.
*Form (when first open).*—Cupped. Permanence—retains its forms to the end, but outer petals curl back.
*Petalage.*—Double (full but open center). Number of petals under normal conditions, 30.
*Color.*—Center of flower—White, Plate 53, with lower half of petals overcast with Sea-foam Yellow, Plate 31. Outer petals—White, Plate 53. Base of petals (aiglet)—Pale Greenish Yellow, Plate 5. Inside of petals—White, Plate 53. Reverse of petals—White, Plate 53. General tonality from a distance—White, Plate 53.
*Discoloration.*—General tonality at end of first day—White, Plate 53. Second day—White, Plate 53. Third day—White, Plate 53.

Petals:
*Texture.*—Leathery; is not affected by wet or hot weather.
*Appearance.*—Inside—satiny. Outside—shiny.
*Form.*—Round.
*Arrangement.*—Imbricated (regularly arranged shingle-like).
*Petaloids in center.*—Few; large.
*Persistence.*—Drop off cleanly.
*Fragrance.*—Moderate. Nature—tea (average hybrid tea scent).
*Lasting quality.*—On the plant—very long. As cut flower—very long.

*Genital organs*

Stamens, anthers: Large; many; regularly arranged around styles. Color—Ochraceous-Buff, Plate 15.
Stamens, filaments (threads): Medium length. Color—Lumiere Green, Plate 17.
Pollen: Color—Pale Ochraceous-Buff, Plate 15.
Styles: Bunched; uneven length; medium length; thin.
Stigmas: Color—Light Chalcedony Yellow, Plate 17.
Ovaries: All enclosed in calyx.
Hips: None.
Seeds: None.

*Plant*

Form: Bush.
Growth: Very vigorous; upright.
Foliage: Compound of 5 to 7 leaflets.
*Size.*—Large.
*Quantity.*—Normal.
*Color.*—New foliage: upper side—Courge Green, Plate 17, with midrib and serrations Carmine, Plate 1; under side—Hellebore Green, Plate 17, lightly overcast with Carmine, Plate 1. Old foliage: upper side—Dark Cress Green, Plate 31; under side—Light Elm Green, Plate 17.
*Shape.*—Oval pointed.
*Texture.*—Upper side—leathery. Under side—rough.
*Ribs and veins.*—Ordinary.
*Edge.*—Serrated (saw-toothed).

*Serration.*—Both double and single; small.

*Leaf stem.*—Color—Water Green, Plate 41. Under side—prickly.

*Stipules.*—Medium length; bearded.

Wood:

*New wood.*—Color—Parrot Green, Plate 6. Bark—smooth.

*Old wood.*—Color—Spinach Green, Plate 5. Bark—smooth.

Thorns:

*Thorns.*—Quantity: on main stalks from base—many; on laterals from stalk—Many. Form—narrow base; medium length; some straight and some hooked downward. Color (when young)—Honey Yellow, Plate 30. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of profuse production of blooms, firm, thick and full flower petals, a distinctive White flower color with a faint touch of cream in the center of the flower, many light-colored thorns, and exceptional suitability for garden use.

No references cited.